United States Patent [19]

Womersley

[11] 4,159,209

[45] Jun. 26, 1979

[54] METAL COMPLEXES

[75] Inventor: Peter Womersley, Stockport, England

[73] Assignee: Manchem Limited, Manchester, England

[21] Appl. No.: 876,301

[22] Filed: Feb. 9, 1978

[51] Int. Cl.² ........................ C07F 7/28; C04B 31/40
[52] U.S. Cl. .......................... 106/308 N; 260/429.3; 260/429.5
[58] Field of Search .......... 260/429.3, 429.5, 448 AD; 106/308 N

[56] References Cited

U.S. PATENT DOCUMENTS

| | | | |
|---|---|---|---|
| 2,824,114 | 2/1958 | Bostwick | 260/429.3 |
| 2,824,115 | 2/1958 | Beacham et al. | 260/429.3 X |
| 2,978,347 | 4/1961 | Koehler et al. | 260/429.3 X |
| 3,458,552 | 7/1969 | Hauck et al. | 260/429.3 X |
| 3,892,791 | 7/1975 | Brook et al. | 260/429.5 |
| 3,981,986 | 9/1976 | Rubino | 260/429.3 |

*Primary Examiner*—Helen M. S. Sneed
*Attorney, Agent, or Firm*—James R. Thornton

[57] ABSTRACT

Metal complexes prepared by the reaction of less than one mole of an alkanolamine with at least one mole of a metal alkoxide and a polyhydric alcohol. The complexes are useful for imparting thixotropy to systems containing protective organic colloids.

16 Claims, No Drawings

METAL COMPLEXES

This invention relates to metal complexes. More specifically, this invention relates to metal complexes which may be used to confer a greater degree of structure to systems containing protective organic colloids, for example, substantially aqueous emulsion paints, solvent based foundry paints, paint strippers and drilling muds.

BACKGROUND OF THE INVENTION

Additives have been proposed, especially for use in aqueous polymer systems containing organic colloids, which can vary the structure of the systems from a creamy consistency to an immobile gel which liquefies under the shearing action of a brush or roller. British patent specification No. 922,456 describes the use of water soluble titanium chelates as additives to impart thixotropy to emulsion compositions having a water-soluble, hydroxyl group-containing organic colloid. British patent specification No. 1,101,427 describes the use of water soluble zirconium or aluminum chelates in similar systems.

An object of this invention is to provide improved metal complexes which can be used to impart thixotropy to aqueous or solvent based systems containing protective organic colloids.

Accordingly, the present invention provides a metal complex prepared by reacting less than 1 mole of an alkanolamine with at least 1 mole of a metal alkoxide or mixture of metal alkoxides, with the remaining reactive sites on the metal complex being occupied by groups derived from a polyhydric alcohol.

The invention also provides a method of preparing the metal complex which comprises reacting less than 1 mole of an alkanolamine with at least 1 mole of a metal alkoxide or mixture of metal alkoxides, and subsequently adding an excess of a polyhydric alcohol. Any remaining monohydric alcohol co-produced by the reaction is removed by distillation to ensure none remains in equilibrium.

The invention further provides an alternative method of preparing the metal complex which comprises adding to at least one metal alkoxide, an excess of a polyhydric alcohol, heating the resulting mixture to remove by distillation the liberated alcohol, and subsequently adding an alkanolamine. The alkanolamine is introduced after the first reaction between the polyhydric alcohol and the metal alkoxide has been completed, preferably below 100° C. as the product is cooling down to about room temperature. The amount of polyhydric alcohol required to give the required excess of alcohol is at least 2 moles of the alcohol per mole of metal present. When dihydric alcohols are used, at least 3 moles of alcohol are required per mole of metal present. In practice, the complex of the present invention is not isolated but is maintained dissolved in a polyhydric alcohol for use as a gelling agent. Usually the alcohol is that utilized in the preparation of the complex.

The metal alkoxides used in the present invention are derived from lower aliphatic alcohols containing up to four carbon atoms, such as methanol, ethanol, n-propanol, isopropanol, n-butanol and sec.butanol. The preferred metals are titanium, aluminum and zirconium. The metal alkoxides can be used alone or as mixtures in the process of manufacture of the complexes. Typical metal alkoxides are the iso-propoxides and butoxides of aluminum, titanium and zirconium.

The alkanolamine used for preparing the metal complexes may be a monoalkanolamine, a dialkanolamine or a trialkanolamine derived from the lower primary alcohols having up to about six carbon atoms, with the trialkanolamines being preferred. In the preparation of the metal complex the proportion of alkanolamine to metal alkoxide is preferably from 0.25 to 0.9 moles alkanolamine to 1 mole of the metal alkoxide.

Examples of polyhydric alcohols include the mono and polyethylene glycols, 1,3-butylene glycol, trimethylene glycol and glycerol. For single metal complexes, polyethylene glycols having average molecular weights of from about 200 to about 400 and glycerol are preferred. Whereas, for mixed metal complexes, diethylene glycol is a preferred alcohol.

When added to organic colloid solutions, the metal complexes according to this invention show improved gelling characteristics over gelling agents previously used. This is attributable to the additional stabilizing effect of the polyhydric alcohols. Although the polyhydric alcohols are weak complexing agents, they are sufficiently strong to delay hydrolysis sufficiently to allow the formation of stronger links with the colloid itself. Metal complexes containing similar molar ratios of metal alkoxide to alkanolamine to those of the present invention but diluted by the presence of monhydric alcohol by-product, give cloudy inferior gels when added to organic colloid solutions.

The organic colloids which are gelled by the complexes of the present invention may be ionic or non-ionic. Anionic colloids are more reactive and consequently the metal must be more strongly complexed in order to provide satisfactory stability. Non-ionic colloids are less reactive towards the metal complexes and therefore can be used with a less strongly bound metal. Examples of organic colloids which are gelled on addition of the metal complexes are cellulose derivatives such as sodium carboxymethyl cellulose, hydroxyethyl cellulose, hydrodypropylmethyl cellulose and methyl cellulose; natural starches and gums and alkali metal and ammonium salts of acrylic acid polymers.

The final loading of the metal complex to the system containing the protective colloid is determined by the degree of structure required in the product. Generally additions of from about 0.25 to 5% by weight of the metal complex to an aqueous emulsion of a film-forming polymer are suitable and particularly suitable are additions of from 0.25 to 2% by weight of the metal complex based on the weight of the emulsion. This range of additions of the metal complex is also typical for the other systems mentioned herein.

By way of example the invention is further described by reference to aqueous film-forming compositions containing protective colloids, particularly emulsion paints. To be useful as additives to emulsion paints to impart thixotropy and having the appropriate rheological properties, complexes must have the combination of essential properties such as stability in aqueous systems over a reasonably wide pH range, e.g. pH 5–11, stability against competing paint ingredients and sufficient residual reactivity to combine with the colloids to give the desired thixotropic gel.

The reactivity of the final complex is dependent upon the relative strength of the particular complexing agent selected. A partial complex based on a strong complexing agent only occupying some of the coordination sites on the metal still leaves sites available for reaction with the colloids in the paint. Weaker complexing agents can be used in excess of the theoretical amount because the bonds formed with the colloid are stronger than those in the original complex.

Emulsion paints conventionally contain, in addition to film-forming polymers or co-polymers, other ingredients such as extenders or fillers, for example barytes, blanc fixe, china clay, mica, talc and whiting; plasticisers and dispersing aids such as sodium hexametaphosphate.

In systems containing sodium hexametaphosphate and/or calcium ions, e.g., derived from whiting, the preferred metal complexes are those containing titanium as the major or only metal ingredient. Titanium complexes show better stability against competition from both sodium hexametaphosphate and calcium ions than the analogous aluminum and zirconium complexes which may preferentially react with phosphate in some systems and precipitate or form unsuitable complexes with calcium. It is therefore preferred to use aluminum or zirconium complexes in systems containing very little or no phosphate or calcium salts.

However, I have found that complexes prepared containing the mixed metals of titanium and aluminum show synergism over the single metal complexes. For paints containing sodium hexametaphosphate, titanium is the main metal ingredient but I have further found that the presence of aluminum up to a molar ratio of 0.25Al/0.75Ti shows improved gelling characteristics over the titanium complex alone. For sodium hexametaphosphate-free paints, molar ratios of 0.95–0.70Al/0.05–0.30Ti have shown improved gelling characteristics as illustrated in the following Example 1.

EXAMPLE 1

Mixed aluminum/titanium complexes containing a total of 1 mole metal, 0.3 moles of triethanolamine and 4 moles of diethylene glycol, were added at equal total metal loadings to a 1% solution of the acrylic colloid Texicryl 13–301. The viscosity of the resulting colloids was measured and the results obtained are recorded in Table I below.

Table I

| Moles Al | 1.00 | 0.95 | 0.90 | 0.85 | 0.80 | 0.75 | 0.70 |
|---|---|---|---|---|---|---|---|
| Moles Ti | 0.00 | 0.05 | 0.10 | 0.15 | 0.20 | 0.25 | 0.30 |
| Viscosity (poises) | 60 | 78 | 87 | 125 | 130 | 125 | 85 |

The ratio of alkanolamine to metal in the complexes is mainly determined by the ionic nature of the colloid. As mentioned in the foregoing, anionic colloids are more reactive and consequently stronger complexes will be required than in the case of non-ionic colloids. The presence of an alkanolamine gives a metal complex of increased strength which is required to provide satisfactory solubility in aqueous systems. The optimum amount of alkanolamine required for maximum gelation varies depending on the paint system. The following Example 2 illustrates the variation in gelling characteristics with the amount of alkanolamine used.

EXAMPLE 2

Metal complexes were prepared comprising 0.2 moles Ti, 0.8 moles Al, 3.5 moles of diethylene glycol and 0.1–0.4 moles of triethanolamine. The resulting metal complexes were added to an emulsion paint formulation free of sodium hexametaphosphate and the viscosities were measured. The results are recorded in Table II below.

Table II

| Moles triethanolamine | 0.10 | 0.15 | 0.20 | 0.25 | 0.30 | 0.35 | 0.40 |
|---|---|---|---|---|---|---|---|
| Viscosity (poises) | 423 | 444 | 523 | 477 | 563 | 482 | 470 |

The mixed complexes of the present invention are preferably manufactured by mixing the alkoxides of the metals in the appropriate molar proportions, adding an excess of polyhydric alcohol as herein defined, and heating, with or without vacuum, at a temperature sufficient to remove the liberated alcohol by distillation. The desired amount of alkanolamine is added after the liberated alcohol has been removed.

Alternatively, single metal complexes may be mixed in the desired proportions to form suitable mixed metal complexes.

The following examples illustrate the preparation of the metal complexes of the invention.

EXAMPLE 3

A reaction vessel was loaded with 204 grams of molten aluminum isopropoxide. 112 grams of triethanolamine were added to the vessel with stirring and the vessel was heated sufficiently to maintain a steady reflux of liberated isopropyl alcohol. 400 grams of polyethylene glycol of av. MW 300 were then added and the refluxing was continued for a further 30 minutes.

Heating was reduced and all the liberated isopropyl alcohol was removed by distillation under reduced pressure.

A further 200 grams of polyethylene glycol were added to the product to provide a metal complex which was easily and homogeneously dispersible in aqueous systems.

On addition of the metal complex to a system containing a water-soluble, polyacrylic colloid, a strong stable gel was obtained.

EXAMPLE 4

The procedure of Example 3 was repeated except that 126 instead of 112 grams of triethanolamine were used.

On the addition of the metal complex product to an aqueous system containing sodium carboxymethyl cellulose a strong, stable gel was obtained.

EXAMPLE 5

The procedure of Example 3 was repeated except that 120 grams instead of 112 grams of triethanolamine were used.

On addition of the complex to aqueous systems containing a polyacrylic colloid or sodium carboxymethyl cellulose and alcoholic systems containing an acrylic colloid, strong stable gels were obtained in each case.

EXAMPLE 6

The procedure of Example 3 was repeated except that 52.5 grams of diethanolamine were employed instead of the 117 grams of triethanolamine.

The metal complex product was suitable for the gelation of aqueous and alcoholic solutions of non-ionic colloids.

EXAMPLE 7

A reaction vessel was loaded with 327 grams of zirconium isopropoxide. 112 grams of triethanolamine were introduced into the vessel with stirring and the vessel was heated until a steady reflux of isopropyl alcohol was maintained. 400 grams of polyethylene glycol of av. MW 300 were added and the refluxing was continued for a further 30 minutes. Heating was reduced and all the liberated isopropyll alcohol was removed by distillation under reduced pressure.

A further 200 grams of polyethylene glycol were added to the product to provide a metal complex which was easily and homogeneously dispersible in aqueous systems.

EXAMPLE 8

41 Grams of aluminum isopropoxide and 179 grams of titanium isopropoxide were mixed together in a reaction vessel. 424 grams of diethylene glycol were added with stirring and the vessel was heated to remove all the liberated isopropyl alcohol by distillation.

The product was allowed to cool and during the cooling cycle 50 grams of triethanolamine were added with stirring.

The metal complex produced was suitable for rendering thixotropic emulsion paints containing phosphates and/or calcium salts.

Similar results are obtained with other alkanolamines such as ethanolamine, isopropanolamine, di-isopropanolamine, butanolamine, and the like.

Various changes and modifications of the invention can be made, and, to the extent that such variations incorporate the spirit of this invention, they are intended to be included within the scope of the appended claims. What is claimed is:

1. A metal complex prepared by reacting less than 1 mole of an alkanolamine with at least 1 mole of a mixture of aluminum and titanium alkoxides, with the remaining active sites on the metal complex being occupied by groups derived from a polyhydric alcohol.

2. A metal complex according to claim 1, wherein the molar proportion of the alkanolamine to the metal alkoxides is within the range 0.25:1 to 0.9:1.

3. A metal complex according to claim 1 wherein the metal alkoxides are derived from an aliphatic alcohol containing up to 4 carbon atoms.

4. A metal complex according to claim 1 wherein the polyhydric alcohol is diethylene glycol.

5. The process for the preparation of a metal complex according to claim 1 which comprises reacting a mixture of aluminum and titanium alkoxides with (i) an excess of a polyhydric alcohol and (ii) with an alkanolamine.

6. The process for the preparation of a metal complex according to claim 1, which comprises reacting less than 1 mole of an alkanolamine with at least 1 mole of a mixture of aluminum and titanium alkoxides, and subsequently adding an excess of a polyhydric alcohol and removing the monohydric alcohol by-product by distillation.

7. The process for the preparation of a metal complex according to claim 1, which comprises adding to a mixture of aluminum and titanium alkoxides an excess of a polyhydric alcohol, heating the resulting mixture to remove by distillation the liberated alcohol and subsequently adding an alkanolamine.

8. The process according to claim 7 wherein the alkanolamine is added after completion of the reaction between the polyhydric alcohol and the metal alkoxides as the product is cooling at a temperature below 100° C.

9. A thixotropic composition containing a film-forming polymer and organic colloid gelled with a metal complex prepared by reacting less than 1 mole of an alkanolamine with at least 1 mole of a mixture of aluminum and titanium alkoxides, with the remaining active sites on the metal complex being occupied by groups derived from a polyhydric alcohol, wherein the molar ratio of said aluminum to titanium in said metal complex is up to 0.25 Al/0.75 Ti, said composition also containing sodium hexametaphosphate and/or calcium ions.

10. A thixotropic composition according to claim 9, comprising from 0.25 to 5% by weight of the metal complex based on the film-forming polymer.

11. A thixotropic composition which is free from sodium hexametaphosphate, containing a film-forming polymer and organic colloid gelled with a metal complex prepared by reacting less than 1 mole of an alkanolamine with at least 1 mole of a mixture of aluminum and titanium alkoxides, with the remaining active sites on the metal complex being occupied by groups derived from a polyhydric alcohol, wherein the aluminum/titanium molar ratio is 0.95–0.7 Al/0.05–0.30 Ti.

12. A thixotropic composition according to claim 9 which is an emulsion paint.

13. A metal complex according to claim 1 containing aluminum in a molar ratio of up to 0.25 Al/0.75 Ti.

14. A metal complex according to claim 1 comprising aluminum and titanium in molar ratios of 0.95–0.7 Al/0.05–0.30 Ti.

15. A metal complex according to claim 1 or 5 in which said alkanolamine is derived from a lower primary alcohol having up to about six carbon atoms.

16. A thixotropic composition according to claim 11, comprising from 0.25 to 5% by weight of the metal complex based on the film-forming polymer.

* * * * *